United States Patent [19]
Mitchell

[11] 3,974,209
[45] Aug. 10, 1976

[54] SUBSTITUTED TERTIARY AMINES AND PROCESSES FOR PREPARING THE SAME

[75] Inventor: Robert S. Mitchell, Webster Groves, Mo.

[73] Assignee: Monsanto Company, St. Louis, Mo.

[22] Filed: Dec. 16, 1974

[21] Appl. No.: 532,963

Related U.S. Application Data

[63] Continuation-in-part of Ser. No. 169,131, Aug. 4, 1971, abandoned.

[52] U.S. Cl. .............................. 260/502.5; 210/57; 252/8.1; 252/8.9; 260/269; 260/270 R; 260/288 R; 260/290 R; 260/326 R; 260/347.7; 260/429 R; 260/429.2; 260/429.7; 260/429.9; 260/431; 260/432; 260/435 R; 260/438.5 R; 260/439 R; 260/448 R; 260/501.12; 260/501.19; 260/926

[51] Int. Cl.$^2$.......................................... C07F 9/38

[58] Field of Search ................................ 260/502.5

[56] References Cited
UNITED STATES PATENTS 2,964,549 12/1960 Ramsey et al. .................. 260/502.5
3,288,846 11/1966 Irani et al. ....................... 260/502.5
3,298,956 1/1967 Irani et al. ....................... 260/502.5

OTHER PUBLICATIONS

Wagner et al., "Synthetic Organic Chemistry", 1953, pp. 226 to 232.

*Primary Examiner*—Joseph E. Evans
*Attorney, Agent, or Firm*—Thomas B. Leslie

[57] ABSTRACT

Substituted tertiary amines of the general formula

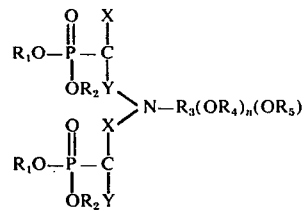

wherein $R_1$, $R_2$, $R_3$, $R_4$, $R_5$, X and Y are hereinafter defined and $n$ is 1 – 20, and which are found useful as agents for complexing metal ions such as in the field of water treating.

4 Claims, No Drawings

SUBSTITUTED TERTIARY AMINES AND PROCESSES FOR PREPARING THE SAME

This application is a continuation-in-part of copending application Ser. No. 169,131 filed Aug. 4, 1971, now abandoned.

The present invention relates to a new class of amine compounds and processes for preparing such compounds. More particularly, the present invention has as its primary object providing substituted tertiary amines and processes for preparing the same.

According to the present invention, there is provided a new and useful class of substituted tertiary amines corresponding to the following formula:

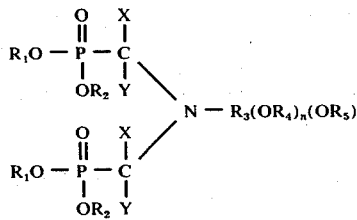
(I)

In Formula I above, $R_1$ and $R_2$ can be alike or unlike and are from the group metal ions and hydrogen and alkyl, alkenyl, aryl, alkyl aryl, cyclic and alicyclic groups. The aforementioned metal ions are from the group of metals which includes, without limitation, alkali metals such as sodium, lithium and potassium; alkaline earth metals, such as calcium and magnesium; aluminum; zinc; cadmium; manganese; nickel, cobalt, cerium; lead; tin; iron; chromium; copper; gold; and mercury. Also included are ammonium ions and alkyl ammonium ions. In particular, those alkyl ammonium ions derived from amines having a low molecular weight, such as below about 300, and more particularly the alkyl amines, alkylene amines, and alkanol amines containing not more than two amine groups, such as ethyl amine, diethyl amine, propyl amine, propylene diamine, hexyl amine, 2-ethylhexyl amine, N-butylethanol amine, triethanol amine, and the like, are the preferred amines. It is to be understood that the preferred metal ions are those which render the compound a water-soluble salt in concentrations sufficient for the desired applications, such as alkali metal ions. Other water-soluble salts are those in which $R_1$ and $R_2$ are ammonium or alkyl ammonium ions described above.

In Formula I, it is to be understood that this includes esters, partial esters, salts, partial salts, acids and partial acids. When $R_1$ and/or $R_2$ is an organic group, the preferred substituents (or groups) are the following:
a. alkyl - containing from about 1 to about 18 carbon atoms;
b. alkenyl - containing from about 1 to about 18 carbon atoms;
c. aryl - phenyl, naphthyl, anthryl, or phenanthryl;
d. alkyl aryl (alkaryl) - hydroxy, halogen, lower alkyl, having from 1 to about 6 carbon atoms, and amino substituted phenyl, naphthyl, anthryl, or phenanthryl;
e. cyclic - containing from about 4 to about 8 carbon atoms and there may be present in the ring either a nitrogen, sulfur, oxygen or phosphorus atom; and
f. alicyclic - containing from about 4 to about 10 carbon atoms.

In Formula I above, $R_3$ is an alkyl group containing from 3 to 5 carbon atoms, such as propyl, butyl and the like. It is preferred that $R_3$ be a propyl group. $R_4$ is an alkyl group containing from 2 to 5 carbon atoms, preferably an ethyl group.

$R_5$ is an alkyl group containing from 1 to 5 carbon atoms; the preferred alkyl group is ethyl.

In Formula I above, X and Y are each alike or unlike and are from the group hydrogen and organic radicals such as alkyl containing less than 40, preferably 1 to 4 carbon atoms. It is to be understood that organic radicals such as other aliphatic groups and also aromatic groups are included herein.

In Formula I, n has a value of from 1 through 20. It is to be understood that all of the compounds falling within the above Formula I and as heretofore defined are generically described herein as "substituted tertiary amines" or "STA". In other words, then, the acids, salts and esters and physical and chemical mixtures thereof are all generically described herein as STA.

Illustrative (but without limitation) of some of the present invention STA are shown below:

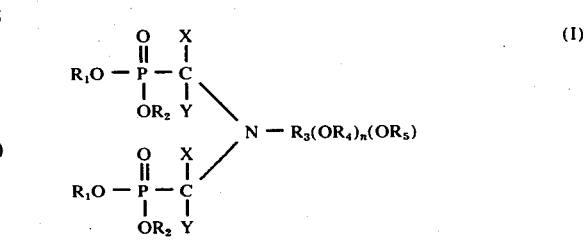
(I)

| Compound Number | $R_1$ | $R_2$ | $R_3$ | $R_4$ | $R_5$ | X | Y | n |
|---|---|---|---|---|---|---|---|---|
| 1 | H | H | $(CH_2)_3$ | $C_2H_4$ | $C_2H_5$ | H | H | 2 |
| 2 | " | " | " | " | " | " | " | 5 |
| 3 | " | " | " | " | " | " | " | 10 |
| 4 | " | " | " | " | " | " | " | 15 |
| 5 | " | " | " | " | " | " | " | 20 |
| 6 | " | " | $(CH_2)_3$ | $C_2H_4$ | $C_2H_5$ | $CH_3$ | $CH_3$ | 2 |
| 7 | " | " | $(CH_2)_4$ | " | " | H | H | 2 |
| 8 | " | " | $(CH_2)_5$ | " | " | " | " | 2 |
| 9 | " | " | $(CH_2)_3$ | $C_3H_6$ | " | " | " | 5 |
| 10 | " | " | " | " | " | " | " | 15 |
| 11 | " | " | $(CH_2)_5$ | $C_4H_8$ | $C_3H_7$ | " | " | 2 |
| 12 | —Zn— | | $(CH_2)_3$ | $C_2H_4$ | $C_2H_5$ | " | " | 2 |
| 13 | $CH_3$ | $CH_3$ | " | " | " | " | " | 2 |
| 14 | H | H | $(CH_2)_3$ | $C_2H_4$ | " | " | " | 1 |
| 15 | $C_2H_5$ | $C_2H_5$ | " | " | " | " | " | 2 |
| 16 | H | H | " | " | $CH_3$ | " | " | 2 |
| 17 | Na | Na | " | " | $C_2H_5$ | " | " | 2 |

In general, the STA are prepared by reacting together under certain conditions,
a. a phosphorus-containing material from the group orthophosphorous acid, a combination of $PCl_3$ and $H_2O$, and a dialkyl phosphite ester,
b. an aldehyde or a ketone, and
c. an (primary) amine having the general formula

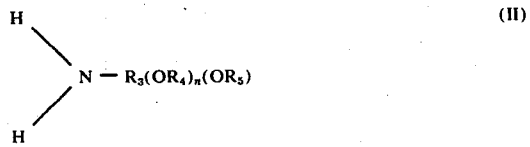
(II)

In Formula II above, $R_3$, $R_4$ and $R_5$ have the same meaning and connotation as set forth in Formula I above.

The compounds falling within Formula II above are designated "amine" or "amines" herein; (these are to be distinguished from the alkyl ammonium ions-amines and STA heretofore mentioned.)

It has been found that by forming a mixture of (a), (b) and (c) and subjecting the mixture to reactive conditions, a STA having two N—C—P linkages can be formed.

The amines, item (c) above, falling within Formula II are, in part, described and prepared according to the processes outlined in "Encyclopedia of Chemical Technology", Kirk-Othmer, 1961 by The Interscience Encyclopedia, Inc. New York; Volume I, pages 702–717 and Volume 11, pages 190–192, and which is incorporated herein by reference. More specifically, these amines are prepared by reacting an alkylene glycol monoalkylether with an unsaturated aliphatic nitrile and then subjecting the reaction product to hydrogenation. For example, ethoxy, ethoxy, ethoxy propyl amine is prepared by reacting diethylene glycol monoethylether with acrylonitrile and then hydrogenating the reaction product. Typical amines falling within Formula II above include (without limitation or restriction):

$$H_2N(CH_2)_3(OC_2H_4)_2(OCH_2CH_3) \quad (III)$$

$$H_2N(CH_2)_3(OC_2H_4)_{10}(OCH_2CH_3) \quad (IV)$$

$$H_2N(CH_2)_3(OC_3H_6)_2(OCH_2CH_3) \quad (V)$$

$$H_2N(CH_2)_5(OC_2H_4)_2(OCH_2CH_3) \quad (VI)$$

$$H_2N(CH_2)_4(OC_2H_4)_5(OCH_2CH_3) \quad (VII)$$

It is to be understood that the amines falling within Formula II can be used in their (a) technical grade form, (b) chemically pure form, or (c) crude form which is obtained directly from the synthesis of the amine.

Aldehydes and ketones (i.e., generically referred to herein as organic carbonyl compounds) that can be used in the processes of this invention to prepare the polyamines include all of those having the formula:

(VIII)

wherein X and Y can be like or unlike, and are selected from the group consisting of hydrogen and organic radicals (heretofore exemplified in the definitions of $R_1$ and $R_2$). When X is hydrogen, the materials represented by Formula VIII is an aldehyde. When both X and Y are organic radicals, it is a ketone. Examples of some of the aldehydes that are useful in the practice of the present invention processes are formaldehyde (such as paraformaldehyde), acetaldehyde, 2-bromoacetaldehyde, caproaldehyde, nicotinaldehyde, crotonaldehyde, 2,2-dichloromalonaldehyde, gluteraldehyde, p-tolunaldehyde, benzaldehyde, 2-furaldehyde, malonaldehyde, phthalaldehyde, 3,5-dibromophthalaldehyde, 1,cyclohexene-1-carboxyaldehyde, 3-quinolinecarboxaldehyde, 3,aminobenzaldehyde, N-(3-formylpropyl) phthalimide, etc. In conjunction with the use of these aldehydes, it is to be understood that they can be used per se or mixed with alcohols in order to, inter alia, facilitate easier handling of the reaction mass, temperature control and the prevention of foaming. For example, if formaldehyde is selected, Formalin, which is a trademark for a 37% (U.S.) or 40% (British) formaldehyde solution, can be used. Generally, these types of solutions contain from about 0% to about 40% methanol.

Typical of the ketones that can be used are acetone, methylethylketone, 2-pentanone, 3-pentanone, 1-chloro-2-propanone, butyrone, 1-bromo-7-nitro-n-heptanone, acetophenone, p-bromo-α-chloroacetophenone, 5,6,7,8-tetrahydro-1-isobutyronapthone, capriphenone, α,α-dimethylstearophenone, 1-cyclohexyl-2-methyl-1-propanone, 1-(2-furyl)-1-butanone, 1-(5-quinolyl)-1-pentanone, 2-acetyl chrysene, 4-bromobenzophenone, 2,4-pentanedione, 3,4-diacetyl-2,5-hexanedione, 3-cyclohexene-1-one, 2(3)-pyridone, 2-acetonyl cyclohexanone, and the like.

Note that the specific examples of aldehydes and ketones presented above do not represent the only such compounds that can be utilized in preparing the novel compounds of the present invention. They are indicative, however, of the very wide range of raw materials that can be used. For example, in the specific examples listed can be found organic radicals such as aliphatic hydrocarbyl, alicyclic, aryl, alkylaryl, hetrocyclic, substituted aliphatic hydrocarbyl, substituted alicyclic, substituted aryl, substituted alkylaryl, and substituted heterocyclic radicals. These radicals can be either saturated or unsaturated, and can contain straight or branched chains. Organic radicals containing "rings", too, are illustrated above. Multi-ring radicals containing 2 to 5, or even more can be utilized to advantage in the practice of the invention.

Because of factors such as steric hindrance, which can become significant when the preparation of relatively high molecular weight STA is undertaken, the aldehydes that find greatest utility in the practice of the invention usually contain no more than 30 carbon atoms, while the ketones that are most broadly used herein usually contain no more than 20 carbon atoms.

When it is desired to prepare the ester form of the compounds falling within Formula I (i.e., where $R_1$ and $R_2$ are organic radicals) above, the corresponding dialkyl phosphite ester, $(RO)_2PHO$, wherein R is an alkyl group containing 1 to 18, preferably 1 to 8, carbon atoms, is used in place of orthophosphorous acid as the phosphorus-containing specie.

Orthophosphorous acid, illustrated by Formula IX is available commercially.

(IX)

For ease of description, orthophosphorous acid will generally be described hereinafter as the phosphorus-containing material reactant.

It can be utilized in the processes of the present invention either as the acid, itself, or in the form of its salts, such as its mono- or di-ammonium salts, and mono- or di-alkali metal salts. When orthophosphorous acid is utilized in the salt form, usually an amount of a supplementary acid sufficient to effectively convert the salt form into the more reactive orthophosphorous acid is used. (The use of these "supplementary" acids in the processes of this invention will be discussed in more detail subsequently.)

It is to be understood that while $H_3PO_3$ is used in this form, the individual ingredients $PCl_3$ and $H_2O$ which react to make $H_3PO_3$ can be used separately, e.g., added at different points of the process operation, or added simultaneously, i.e., two individual feed streams at the same time.

Ordinarily, for at least one from each of the reacting materials, i.e., items (a), (b) and (c) above, to undergo an interreaction to form one of the STA, they must simply be mixed together in certain relative proportions (the relative proportions will be described in more detail below), preferably in an acidic aqueous medium, and ordinarily subjected to an elevated temperature for a sufficient period of time to achieve the desired reaction. At room temperature, the rate of interreaction of these materials is slow. (Where time is not a factor, then, the reaction can be carried out at 25°C or lower.) Increasing the temperature generally results in increasing the rate of the desired reaction, so that, usually, if the temperature of a mixture of phosphorous acid, an amine of Formula II above, and an aldehyde or ketone is above about 70°C, the rate of their interreaction is sufficiently high so that conventional mixing and handling equipment can be utilized to produce the STA continuously and at a commercially practical cost, if desired. It has also been found that increasing the reaction temperature for the processes of this invention (in the temperature range above about 75°C up to about 200°C [the latter being the spontaneous decomposition temperature of orthophosphorous acid at atmospheric pressure]) results in a fairly rapid increase in the rate of the desired reaction. Thus, for practical purposes, it is preferred that reaction temperatures for the formation of the STA wherein orthophosphorous acid is utilized according to the processes of this invention, be above about 85°C. Temperatures within this preferred range (i.e., about 85°C to about 200°C) can readily be maintained by refluxing the aqueous reaction mixture at, above or below atmospheric pressure until the desired reaction has been completed.

It is believed surprising that the pH of the reaction medium has apparently an important influence upon the rate of the desired reaction. For example, it has been found that the rate of the desired reaction in mixtures (containing an amine, formaldehyde, and orthophosphorous acid in the molar ratio, respectively, of about 1:2:2) having a pH above about 4 is low. Perhaps one reason for the low rate of the desired reaction in reaction media having pH's above about 4 is that apparently in these systems a competing reaction (the oxidation of orthophosphorous acid to orthophosphoric acid) takes precedence over the desired interreaction of orthophosphorous acid with the aldehyde or ketone and an amine. Actually, it is preferred that the pH of the reaction mixture (of orthophosphorous acid plus aldehyde or ketone plus and amine, and usually at least some water) be below about 4 and preferably about 2 in order to achieve optimum results in the practice of the present invention. When one of the salts of orthophosphorous acid is utilized as a raw material, and when the ratio of reactive amine to orthophosphorous acid in the reaction mixture is relatively high, the "natural", or usual pH of the reaction mixture or reaction medium is generally not within the preferred range. However, the pH of the reaction medium can be adjusted into the most effective range by adding to the system any of the conventional acids having the ability to lower the pH of the reaction medium. For example, hydrochloric, sulfuric, hydrobromic, phosphoric, and sulfonic acids, as well as many others can be utilized for this purpose. Another example of providing a low pH and also a halide ion for a catalyst (hereinafter discussed) is the use of a halide salt and an acid. These two ingredients alone accomplish the desired result; however, they may react together to form a salt and a hydrogen halide which also achieves the end result. For example, the use of sodium chloride and sulfuric acid results in the formation of sodium bisulfate and hydrogen chloride.

Ordinarily the desired reaction will be fairly complete, under optimum reaction conditions in a reasonable and practical period of time, for example, in less than about 3 hours, when the relatively low molecular weight STA are being prepared. Generally when relatively lower reaction temperatures and when the relatively higher molecular weight aldehydes and ketones are utilized (as raw materials) in the processes herein contemplated, somewhat longer reaction times are required in order to produce optimum yields of the desired products. However, usually no more than about 5 to about 7 hours should be required for the desired reaction to be completed under good reaction conditions, no matter which of the above-described raw materials is utilized. On the average, it can be said that, under optimum reaction conditions, generally from about several minutes to about 3 hours is required in order to produce fairly pure STA products.

It was mentioned heretofore that usually at least some water is present in the reaction medium. While it is not essential that water must be present therein, it has been found that the presence of at least some water contributes substantially to such factors (during and after the reaction) as keeping the reactants in solution, ease of handling of the reaction medium, ease of maintaining the desired reaction temperature (by refluxing, as described above), ease of maintaining adequate heat transfer within the reaction mixture, decreasing the viscosity of the reaction products, etc. Thus, it is desirable that at least about 5 weight per cent of water (based on the total weight of the raw reaction materials charged into the reaction mixture), and preferably at least about 15 weight per cent of water be present in the reaction mixture before it has been exposed to temperatures above about 90 °C for any extended period of time. Additional water can also be added to the reaction medium from time to time if and as it is needed.

The processes of this invention can be carried out with conventional, readily available chemical processing equipment. For example, a conventional heated glass-lined mixing (reaction) vessel fitted with a reflux condenser and a fairly efficient stirrer can be advantageously utilized in practicing any of the preferred embodiments of the invention described in the examples below.

The orthophosphorous acid, amine, and aldehydes or ketones with which this invention is concerned can be intermixed in several manipulative manners without detracting appreciably from the benefits that can be derived from the invention. For example, they can be simply poured together in the appropriate proportions (which proportion will be discussed below) into a mixing vessel, blended, and then heated to the reaction temperature. Or the ingredients can be warmed individually, before they are intermixed. (This particular procedure is useful when higher molecular weight, solid aldehydes and ketones are utilized. Thus, they can be melted before they are placed into the reaction vessel.) The amine can be utilized per se or in the form of its salts such as the HCl salt form thereof. Sometimes it is convenient and desirable to intermix the amine with the phosphorous acid before they are heated very much above ambient temperatures; especially when the amine is not utilized in the form of salts.

When aldehydes or ketones having boiling points below the temperatures at which this invention is practiced are utilized in the practice of the invention usually significantly better yields of the desirable STA (based on the amount of aldehyde or ketone charged into the reaction vessel), can be attained if the aldehyde or ketone is added slowly (e.g., from about 10 minutes to about 3 hours) to the mixture of orthophosphorous acid and amine while the temperature of said mixture is within the desired range. For example, when an aqueous mixture consisting of one mole of ethoxy, ethoxy, ethoxy propylamine, i.e., $CH_3CH_2OCH_2CH_2OCH_2C-H_2O(CH_2)_3NH_2$, two moles of orthophosphorous acid, and two moles of formaldehyde [calculated theoretically to result in the production of one mole of ethoxy, ethoxy, ethoxy propylamino di(methylene phosphonic acid) — Compound No. 1 above] is held at about 100°–110°C for an extended period of time (in order to assure "complete" reaction), less than 0.5 moles of the desired product is made. However, if the same amount of formaldehyde is added slowly (i.e., over a period of about 65 minutes) to a blend of the same amount of water, one mole of ethoxy, ethoxy, ethoxy propylamine and two moles of phosphorous acid held at a temperature of about 100°–110°C, more than 0.50 moles of the desired product is produced. Thus, in the practice of this invention, the addition of the aldehyde or ketone slowly to a hot mixture of phosphorous acid and the amine is a particularly preferred embodiment.

The present invention STA result from reacting (a) the phosphorus-containing material, e.g., orthophosphorous acid and (b) an aldehyde or a ketone with (c) an amine in a molar ratio of at least two moles of (a) and (b) for each mole of (c), the amine. In processes of the present invention, excess aldehyde or ketone (over the necessary 2:1 molar ratio of aldehyde or ketone to amine) can sometimes be utilized to advantage. An excess of orthophosphorous acid, e.g., from about 1% to about 100% by weight, can also be utilized in these processes. However, if the molar ratio of the amine to orthophosphorous acid and aldehyde or ketone is raised above 1:2:2, respectively, there may result side reaction products. Thus, when it is desired to produce a relatively pure STA according to the processes of the present invention, it is preferred that the molar ratio of the amine to orthophosphorous acid, respectively, in the reaction mixture be about 1:2, and that the molar ratio of the amine to aldehyde or ketone, respectively, in the reaction mixture be about 1:2.

One reason why yields of the desirable STA are generally not usually 100% of theory in the processes of this invention is that, in addition to the desired N—C—P linkage-forming reaction, the orthophosphorous acid also undergoes an oxidation reaction (to form orthophosphoric acid) under the conditions that usually favor the desired reaction. Since in most instances the presence of orthophosphoric acid in the final STA products is not particularly detrimental, the inclusion of excess orthophosphorous acid into the reaction medium is generally all that is necessary to make up for this "loss" of orthophosphorus acid from the desired reaction. (Use of excess acid, however, is presently expensive.) However, it has now been discovered that the presence of at least a catalytic amount of halide ions in the reaction mixture (of amine, orthophosphorous acid, aldehyde or ketone, and usually water) inhibits the oxidation of orthophosphorous acid to orthophosphoric acid, and thus makes it possible to produce relatively more of the desired STA product from a given reaction mixture than could otherwise be produced in the absence of halide ions therefrom. Apparently, any simple halide ion can be utilized to accomplish the inhibition described above, although for economic purposes chloride is preferred. The halide ion can apparently be introduced into the reaction mixture in any way whatever without detracting significantly from the benefits that can be derived from practicing the invention, provided it is introduced thereinto before the temperature of the reaction mixture has been heated to or held at about 70°C for more than a few minutes. For example, it can be added in the form of a hydrohalide acid such as HCl, HBr, HI, etc., or as an inorganic salt, such as NaCl, KCl, NaBr, $CaCl_2$, and the like. Another convenient way is as the hydrogen chloride salt of the amine. As mentioned earlier, a mixture of a nonhalide containing acid and halide salt can be used to achieve the desired end result. Even very small amounts of halide ions in the reaction mixture have been found to inhibit the oxidation of orthophoshorous acid to some extent. Excellent results can be accomplished when there is utilized in the reaction mixture between about 0.01 and about 10, and preferably at least about 0.5 weight percent of halide ions. Halide ions in excess of these amounts can be present without any apparent detrimental effects on the processes of the invention. However, as a practical matter, generally, not more than about 20 weight per cent of halide ions is utilized in the processes.

The acid and salt forms of the STA falling within Formula I of the present invention have unique utility in the field of treating water or aqueous systems and function as both a sequestering agent and as a "threshold" agent. It is to be understood that the term threshold as utilized herein refers to the chemical and/or physical phenomenon that less than stoichiometric quantities of the particular STA can effectively prevent the precipitation and/or alter the crystal forms of various salts of metallic ions such as calcium, iron, copper and cobalt. In other words; the threshold treatment of water is that technique by means of which less than stoichiometric quantities of the treating agent are added to interfere with the growth of crystal nuclei and thereby prevent the deposition of insoluble deposits. The term is applied, for example, to the treatment of water with polyphosphates and is discussed in references such as U.S. Pat. No. 2,038,316, and the article by Reitmeier and Buehrer in the Journal of Physical Chemistry, Vol. 44, pages 535 to 574 (1939). An additional explanation of the threshold effect will be found in the publications of Hatch and Rice appearing in Industrial Engineering and Chemistry of January, 1939, and August, 1945. All of the aforementioned publications are to be considered as incorporated herein by reference.

The acid and ester forms of the STA falling within Formula I have unique utility in the field of flame retardancy for cellulosic materials and specifically function as flame retardants therefor.

In the following examples, all parts are by weight unless otherwise specified.

EXAMPLE I

Into a 1-liter flask equipped with a water condenser and dropping funnel are charged approximately 270 grams (1.65 moles) of 50% orthophosphorous acid (and which contained 25.6 grams of HCl) and 84 grams of 37% hydrochloric acid. The total moles of HCl is 1.56. The resultant mixture in the one liter flask is then heated by the addition thereto of approximately 126.0 grams (0.66 moles) ethoxy, ethoxy, ethoxy propyl amine, $H_2N(CH_2)_3(OC_2H_4)_2(OC_2H_5)$, in its technical grade form. This amine is added over a period of approximately 28 minutes at the end of which time, the reaction mass has a temperature of about 72°C. The reaction mass is then heated for 20 minutes to bring it up to boiling thereby obtaining a homogeneous, clear solution having a boiling point of approximately 112°C.

The resultant clear solution in the flask is maintained at boiling, and over a period of approximately 2.25 hours, approximately 52 grams (1.57 moles) of paraformaldehyde is added. At the end of the 2.25 hour period, the reaction mixture, which is a clear solution, is held at boiling with reflux for an additional 1 hour and then is cooled to 25°C. At 25°C, the solution is found to be clear with an amber color. A small portion of this solution is subjected to a steaming step (direct contact) in order to remove chloride impurities. Both portions of said solution are analyzed, utilizing the $P^{31}$ Nuclear Magnetic Resonance spectra (NMR) (which shows the presence of N—C—P linkage) and elemental analysis, and both partial solutions showed the presence of a tertiary amine having the following structural formula:

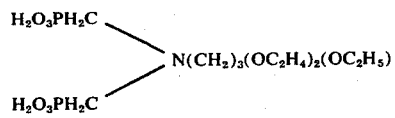

EXAMPLE II

Into a 1-liter flask equipped with a water condenser and dropping funnel are charged approximately 164 grams (1 mole) of 50% orthophosphorous acid and 49.2 grams (0.5 moles) of 37% hydrochloric acid. The resultant mixture in the 1-liter flask is then heated by exothermic reaction while adding approximately 271.5 grams (0.5 moles) of the amine having the formula $H_2N(CH_2)_3)OC_2H_4)_{10}OC_2H_5)$. This amine is added over a period of approximately 30 minutes, at the end of which time, the reaction mass has a temperature of about 70°C. The resultant material is a clear homogeneous solution.

The resultant clear solution in the flask is heated to boiling—about 115°C, and over a period of approximately 2 hours 33 grams (1.0 mole) of commercial paraformaldehyde is added. At the end of the 2-hour period, the reaction mixture, which is a clear, amber solution is held at boiling for 1 hour and then is cooled to 25°C. This solution is analyzed, utilizing the $P^{31}$ Nuclear Magnetic Resonance spectra (NMR) (which shows the presence of N—C—P linkage) and elemental analysis, and shows the presence of a tertiary amine having the following structural formula:

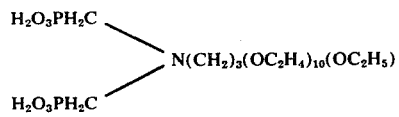

EXAMPLES III – V

Compound Nos. 2, 4 and 14 heretofore set in the specification are prepared in the same manner as used in Examples I and II above with the exception that the starting amine compound is different than those used in Examples I and II.

EXAMPLE VI

Into a 1-liter flask equipped with a water condenser and dropping funnel are charged approximately 164 grams (1.0 mole) of 50% orthophosphorous acid and 49.2 grams (0.5 moles) of a 37% hydrochloric acid. The resultant mixture in the 1-liter flask is then heated by exothermic reaction while adding approximately 109 grams (0.5 moles) of the amine having the structural formula:

$H_2N(CH_2)_5(OC_2H_4)_2(OC_2H_5)$

This amine is added over a period of approximately 30 minutes, after which time a clear homogeneous solution is formed.

The resultant clear solution in the flask is heated to boiling 112°–115°C, and over a period of approximately 3 hours 109.5 grams (0.5 moles) of commercial grade paraformaldehyde is added. At the end of the 3-hour period, the reaction mixture is held at boiling for 1 hour and then cooled to 25°C. The cooled reaction mixture is analyzed, utilizing the $P^{31}$ Nuclear Magnetic Resonance spectra (NMR) (which shows the presence of N—C—P linkage) and elemental analysis and shows the formation of a tertiary amine having the following structural formula:

$(H_2O_3PH_2C)_2N(CH_2)_5(OC_2H_4)_2)OC_2H_5$

EXAMPLE VII

Into a ½-liter flask equipped with a water condenser and dropping funnel are charged approximately 164 grams (1.0 mole) of 50% orthophosphorous acid and 49.2 grams (0.5 moles) of 37% hydrochloric acid. The resultant mixture in the halfliter flask is then heated by exothermic reaction while adding approximately 73.5 grams (0.5 moles) of the amine having the structural formula:

$H_2N(CH_2)_3(OC_2H_4)(OC_2H_5)$

This is added over a period of approximately 30 minutes after which time a clear homogeneous solution is formed.

The resultant clear solution in the flask is heated to boiling, 109°–112°C, and over a period of approximately 3 hours 109.5 grams (0.5 moles) of commercial grade paraformaldehyde is added. At the end of the 3-hour period, the reaction mixture is held at boiling for 1 hour and then cooled to 25°C. The cooled reaction mixture is analyzed, utilizing the $P^{31}$ Nuclear Magnetic Resonance spectra (NMR) (which shows the presence of N—C—P linkage) and elemental analysis and shows the formation of a tertiary amine having the following structural formula:

$(H_2O_3PH_2C)_2N(CH_2)_3(OC_2H_4)(OC_2H_5)$

Salts of the various substituted tertiary amines falling within Formula I above can be made by simply neutralizing any of these amines with a base that contains essentially the desired cation. For example, to make a sodium salt, one of the said tertiary amines can be neutralized with a base containing the sodium cation, such as NaOH, $Na_2CO_3$, and the like, and in same manner with a calcium or ammonium containing base, such as $Ca(OH)_2$, $Ca(SO_4)_2$, $NH_4OH$ or $(NH_4)_2CO_3$, and the like to produce calcium or ammonium salts.

EXAMPLE VIII

In order to demonstrate the utility of the substituted tertiary amines falling within Formula I above, the compounds identified above as Nos. 1 through 12, 14, 16 and 17 are subjected to the sequestration procedure described in the book COORDINATION CHEMISTRY, "Calcium Complexing By Phosphorus Compounds", by C. F. Callis, A. F. Kerst and J. W. Lyons, pages 223–240, Plenum Press, 1969.

Approximately 1 gram of each of the above described compounds (substituted tertiary amines — "sequestration agents") is individually and separately mixed with 0.1% by weight sodium oxalate in a 2-liter flask containing 100 milliliters of water. The pH in each case is adjusted by the addition of sodium hydroxide to a pH 11. Into each solution containing the separate and individual sequestration agents there is titrated a 0.1 molar calcium nitrate solution via the use of a Sargent-Malmstadt automatic titrator, Model SE, and which also measures the turbidity by light transmission. The amount of calcium nitrate solution added to each flask is sufficient to provide ample data to plot the point of inflection at which the sequestrant-containing solution goes from a relatively clear solution to a turbid one. This inflection point is then indicative of the amount of calcium that is sequestered by the particular sequestration agent.

The results of the sequestration test on compounds Nos. 1 through 12, 14, 16 and 17 show that the various tertiary amines are good sequestrants for calcium which is one of the major undesirable cations in water which is used, for example, in cooling towers. Specifically, it is found that 100 grams of the tertiary amine (compound No. 1) prepared in Example I sequesters approximately 1.6 grams of calcium. It is also found that the other tertiary amines (compound Nos. 2 through 12, 14, 16 and 17) sequester calcium in the range of from about 0.3 grams to about 4.8 grams of calcium per 100 grams of the tertiary amine.

Thus, one of the unique applications of the tertiary amine falling within Formula I is their use as a sequestration agent in treating aqueous systems containing calcium ions and which treatment would prevent the formation of calcium salts therein.

EXAMPLE IX

In order to demonstrate the utility of the substituted tertiary amines falling within Formula I above as threshold water treating agents, the ability to prevent precipitation of calcium sulfate by Compound No. 1 is shown. Solutions containing a large quantity of $CaSO_4$ are prepared; Solution A as a control solution and Solution B containing in addition 5 parts per million, based on a 100% active phosphonic acid basis, of ethoxy, ethoxy, ethoxy propylamino di(methylene phosphonic acid), (Compound No. 1). Solution A is prepared by adding to water a concentrated aqueous solution of calcium chloride followed by addition of a concentrated solution of sodium sulfate in sufficient quantities to produce a solution of 10,000 ppm of $CaSO_4$ and then adjusting the pH to 7 with either HCl or NaOH as required. Solution B is prepared in the same manner except that the appropriate amount of the phosphonic acid substituted tertiary amine to produce a 5 ppm concentration is first dissolved in the water prior to addition of the calcium chloride and sodium sulfate. The solutions are stored with continuous agitation at 25°C. for extended periods for carrying out the tests.

The tests show that control Solution A begins to precipitate CaSOPhd 4 within a few minutes after preparation thereof, in 5 hours some 40% of the original 10,000 ppm is precipitated out of solution and in 24 hours the solution substantially reaches an equilibrium saturated concentration at 25°C. of 3600 ppm $CaSO_4$ (36% of the original total present). In contrast, Solution B containing 5 ppm of Compound No. 1 remains clear for at least 24 hours maintaining in solution after 5 hours 100% of the total $CaSO_4$, 92% of total $CaSO_4$ after 24 hours, 85% after 2 days, 67% after 3 days and 54% after 6 days. The concentrations of calcium ions are determined by titration of a sample of each solution with a standard solution of ethylene diamine tetraacetic acid using Eriochrome Black T as indicator.

When the same test is carried out with Solution C prepared in the same manner as above, but containing 5 ppm (on an active phosphonic acid basis) of ethanolamino di(methylene phosphonic acid), a substituted tertiary amine containing a terminal hydroxyl group and derived from ethanol amine in the same manner as the STA's of Formula I, the results are in distinct contrast to the above. After 5 hours pronounced precipitation of $CaSO_4$ is observed, the solution containing only 86% of the total original $CaSO_4$ and after 24 hours cannot be distinguished from the substantially fully precipitated control Solution A, Solution C containing only 38% of the total original $CaSO_4$. This concentration is only 3% above the control concentration of Solution A and indicates substantially no threshold effect.

EXAMPLE X

In order to demonstrate the utility of the esters of the tertiary amines falling within Formula I, approximately 50 grams of the tetraethyl ester of Compound No. 1 (Compound No. 15) are mixed with an inert solvent (carbon tetrachloride) in a 500 milliliter beaker in order to prepare a 10% by weight solution of said ester. After the slurry is prepared, a separate and individual swatch of a 3 × 3 inch undyed cotton cellulose is intimately contacted with the slurry by submerging such swatch in the slurry for approximately 5 minutes. The swatch is withdrawn from the beaker containing this slurry and is dried for 14 minutes in an oven which is maintained at a temperature of approximately 85°C. After a lapse of fourteen minutes at 85°C., the temperature is elevated and the swatch is then subjected to a temperature of approximately 150°C. for 10 minutes in order to "set up" a reaction between the specific ester with the surface groups on the cotton cellulose.

The dried swatch of "treated" cotton is tested for flame retardancy by positioning the swatch over a bunsen burner. The flame is adjusted to a point at which the tip of the flame is approximately 1 inch beneath the treated cotton swatch; an "untreated" cotton swatch is used as a control for comparative purposes. The flame underneath each of the individual cotton swatches (including the control) is maintained for approximately 30 seconds, and then is removed. Visual observations are made. This test shows that the control sample, i.e., the cotton swatch which is not treated with any ester, is completely destroyed. However, with the treated cotton swatch, there is primarily only charring, and the flame on the material is extinguished within about 11 seconds upon the removal of the bunsen burner away from the cotton swatch. Esters of the acid forms of Compound Nos. 2–11, and 14 are tested in a similar fashion and are found to provide fire retardance for cellulosic materials. Thus, it can readily be seen that one of the unique applications of the esters of the substituted tertiary amines falling within Formula I is their use as a fire retardant for cellulose material, for example, cotton clothing.

The above examples have been described in the foregoing specification for the purpose of illustration and not limitation. Many other modifications and ramifications will naturally suggest themselves to those skilled in the art based on this disclosure. These are intended to be comprehended as within the scope of this invention.

What is claimed is:

1. A substituted tertiary amine having the general formula

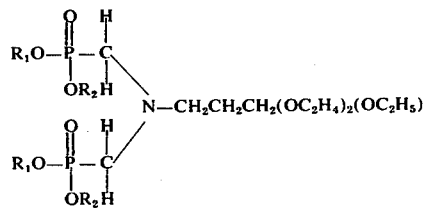

wherein $R_1$ and $R_2$ are alike or unlike and are each independently selected from the group consisting of alkali metal ions, hydrogen and ammonium ions.

2. The amine of claim 1 wherein $R_1$ and $R_2$ are alkali metal ions.

3. The amine as set forth in claim 1 wherein $R_1$ and $R_2$ are each ammonium ions.

4. A substituted tertiary amine having the formula

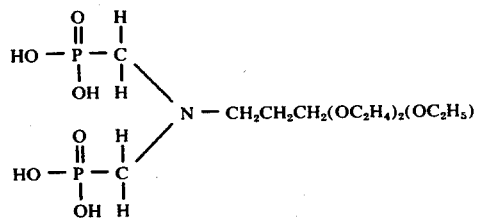

* * * * *